United States Patent [19]

Brule et al.

[11] Patent Number: 5,219,735
[45] Date of Patent: * Jun. 15, 1993

[54] NON-PHOSPHORYLATED PEPTIDES FROM CASEIN-BASED MATERIAL

[75] Inventors: Gérard Brule; Loïc Roger, both of Rennes; Jacques Fauquant, Monfort; Michel Piot, Rennes, all of France

[73] Assignee: Institut National de la Recherche Agronomique, Paris, France

[*] Notice: The portion of the term of this patent subsequent to Nov. 9, 1999 has been disclaimed.

[21] Appl. No.: 599,102

[22] Filed: Oct. 17, 1990

Related U.S. Application Data

[63] Continuation of Ser. No. 734,750, May 15, 1985, Pat. No. 4,980,450, which is a continuation of Ser. No. 418,600, Sep. 16, 1982, abandoned, which is a continuation of Ser. No. 229,075, Jan. 21, 1981, Pat. No. 4,361,587.

[30] Foreign Application Priority Data

Feb. 1, 1980 [FR] France .................... 80 02280

[51] Int. Cl.$^5$ .................... C12P 21/06; A23J 3/00; C07K 1/00; A61K 37/18
[52] U.S. Cl. .................... 435/68.1; 426/42; 426/657; 426/491; 435/272; 514/2; 514/6; 514/7; 530/352
[58] Field of Search .............. 435/68.1, 272; 426/34, 426/42, 657, 491; 424/115, 535; 530/200, 352, 360; 514/2, 6, 7

[56] References Cited

U.S. PATENT DOCUMENTS

| | | | |
|---|---|---|---|
| 3,974,294 | 8/1976 | Schwille et al. | 426/42 X |
| 4,358,465 | 11/1982 | Brule et al. | 435/68.1 |
| 4,361,587 | 11/1982 | Brule et al. | 435/68.1 |
| 4,495,176 | 1/1985 | Brule et al. | 435/68.1 X |
| 4,740,462 | 4/1988 | Brule et al. | 435/68.1 |
| 4,816,398 | 3/1989 | Brule et al. | 435/68.1 |
| 4,980,450 | 12/1990 | Brule et al. | 530/360 X |

OTHER PUBLICATIONS

Mellander, O., Pediatric Clinic and the Institute of Medical Chemistry University of Uppsula, Sweden, 1949, pp. 247–255.

West, D. W., J. Da. Res., vol. 44, No. 2, 1977, pp. 373–376.

Porter, et al., Chem. Tech. 1971, pp. 56–63.

*Primary Examiner*—David M. Naff
*Attorney, Agent, or Firm*—Oblon, Spivak, McClelland, Maier & Neustadt

[57] ABSTRACT

Nonphosphorylated peptides and phosphopeptides useful as alimentary products or medicaments are produced by proteolytic enzyme hydrolysis of a casein-based material. Membrane ultrafiltration is used to separate phosphopeptides which are retained by the membrane in a retentate from the nonphosphorylated peptides which pass through the membrane in an ultrafiltrate. The phosphopeptides in the retentate are disaggregated and are subjected to further membrane ultrafiltration where the phosphopeptides pass through the membrane and are separated from the enzyme. The phosphopeptides form salts, which have dietetic uses, with macroelements such as calcium and/or magnesium and/or oligoelements such as iron and zinc.

11 Claims, 3 Drawing Sheets

NON-PHOSPHORYLATED PEPTIDES FROM CASEIN-BASED MATERIAL

This is a continuation of application Ser. No. 06/734,750, filed on May 15, 1985, now U.S. Pat. No. 4,980,450; which is a continuation of Ser. No. 06/418,600 filed on Sep. 16, 1982, now abandoned; which is a continuation of Ser. No. 06/229,075 filed on Jan. 21, 1981, now U.S. Pat. No. 4,361,587.

The present invention relates to the field of processing casein-based materials. More particularly, it has for its object a method for treating such a material containing phosphocaseinates of bivalent cations, such as calcium and/or magnesium phosphocaseinates. Such substances are found, for example, in milk or in dairy raw materials such as retentates from milk ultrafiltration. The invention also relates to the products obtained by such a method, especially phosphopeptides and non phosphorylated peptides. The invention further encompasses the applications of the thus obtained products and especially of said phosphopeptides, which can be used in the alimentation field to meet specific nutritional requirements. Said phosphopeptides are also useful as medicines.

It is known that the caseins of dairy raw materials, and most particularly of milk, contain phosphoserines which impart to the peptides wherein they occur valuable physico-chemical, technological and physiological properties. Among others, information on milk proteins will be found in the work by Mc KENZIE H. A. (1971) entitled "Milk proteins", Vol. 1 and 2, Academic Press, New York.

Due to the recent advancement as regards both the apparatuses and the understanding of the observed phenomena, membrane ultrafiltration has found broad acceptance in the milk industry, for milk treatment (see, for example, Maubois J. L., Mocquot G. (1971)—Préparation de fromages à partir de preé-fromages liquides obtenus par ultra-filtration du lait "LE LAIT", fascicule 51 508, 495–533). As the milk flows across the ultrafiltration membrane, the water, soluble mineral salts, lactose, low molecular weight nitrogeneous compounds (peptides, free amino-acids) and water-soluble vitamins will flow through the membrane as an ultrafiltrate or permeate, while the proteins and associated components (calcium, phosphorus), fat globules and lipophilous elements will be retained, their concentration increasing as aqueous phase removal proceeds; these form the retentate or proteic concentrate. Obtention of high purity proteic concentrates requires both an ultrafiltration step and a diafiltration step. In the diafiltration step, addition of water or a salt-containing aqueous solution is effected, in continuous or discontinuous manner, into the ultrafiltration retentate. Simultaneously or subsequently, an equivalent amount of permeate is removed. The result of such operation is to deplete the retentate of filterable elements. The advantage of the membrane ultrafiltration technique is to keep milk proteins under the native form.

The method of the invention takes advantage of membrane ultrafiltration to effect fractionating of the components of the casein based raw materials, but by combining said ultrafiltration step with an enzymatic hydrolysis step.

A number of methods are known for the hydrolysis of proteins, e.g. milk proteins. In fact acid hydrolysis does permit to obtain free amino-acids solutions but will destroy some of the latter. Alcaline hydrolysis will preserve tryptophane, but cause an insolubilization which substantially reduces the nutritional value of the initial proteic concentrates.

Enzymatic proteolysis has been known and used for quite a long while for analytic or nutritional purposes, the main object being to solubilize the proteins. Abundant reports will be found in literature on numerous alimentary uses of soybean protein hydrolyzates [See ARAI. S.,NOGUCHI M., KUROSAWA S., KATO H. and FUJIMAKI M. (1970) Applying proteolytic enzymes on soybean, 6-Deodorization effect-], of fish proteins: [see HEVIA P., WHITAKER J. R. and OLCOTT H. S. (1976)-Solubilization of a fish protein concentrate with proteolytic enzymes. J. Agric. Food Chem. Vol 24 (2) 383–385, or of colza, by action of animal, microbial or vegetable proteases.

However, application of those techniques to milk proteins on a commercial scale is still quite limited.

Enzymatic proteolysis is free from the drawbacks of the chemical processes. Conditions of hydrolysis are moderate and thus preserve the nutritional value of the products.

Generally, hydrolysis leads to peptides having a pronounced bitter taste. This effect acts to limit the use of such hydrolyzates for human alimentation. The degree of bitterness of an hydrolyzate is mainly dependent on the nature of the proteic substrate and the enzyme specificity. To remove the bittertaste, it was suggested to use the action of exopeptidases. See for example ARAI S., YAMASHITA M., KATO H., FUJIMAKI M. (1970)-Agric. Biol. Chem. 34, 729, as well as CLEGG K. M., SMITH G. and WALKER A. L. (1974)-Production of an enzymatic hydrolyzate of casein on a kilogram scale. J. Food Technol. 9, 425–431. It was also proposed to modify the peptides by addition of glutamic acids before the plasteic reaction. It is also possible to proceed by removal of the hydrophobous amino-acids.

However, all these known techniques are unsatisfactory and unfit to meet the requirements of the invention. In fact, an extensive solubilization, caused by the use of exopeptidase, will increase the amount of free amino-acids and especially of arginine, lysine, tyrosine, valine, phenylalanine, methionine and leucine, and the net result thereof would be to burden the systems for free amino-acids transport at the intestinal barrier, thus causing a reduction in the nutritional efficiency of the hydrolyzates. On the other hand, the intrinsic quality of the hydrolyzates will be modified since the amino-acid equilbrium itself is changed, this requiring additional provision of free amino-acids.

From the technological standpoint, enzymatic hydrolysis is most usually effected with a discontinuous reactor system. The enzyme is added to the proteic solution to be treated. After a more or less prolonged residence time, in conditions promoting enzymatic activity and substrate attack, the pH is modified and the enzyme is deactivated by a mild thermal treatment. Centrifugation may be effected to remove the undigested insoluble fraction. However, according to this technique of discontinuous enzymatic hydrolysis reaction, it is difficult to use a high enzyme to substrate ratio. Now, it is known, see ROBINS R. C. (1978)—Effect of ratio of enzymes to substrate on amino acid patterns released from proteins in vitro. Internat. J. Vit. Nutr. Res. 48, 44–52, that the enzymes to substrate ratio has a critical influence of the nature of the free amino-acids and peptides released during proteolysis. With a discontinuous process, the enzymes must be destroyed at completion of hydrolysis when provided in excess, as would be compulsory with the aforesaid high ratios.

It was also proposed to use reactors with fixed enzymes. However, these are attended by substantial drawbacks from the practical standpoint. As a matter of fact, the optimum conditions for enzyme activity, especially pH conditions, are shifting, so that the reactor operation is not satisfactory at all times. Moreover, it occurs bacteriological problems, plugging of the fixation beds as well as protein adsorption onto the substrate. In addition the enzymatic reaction tends to get inhibited as time elapses, due to the formation of an enzyme-proteic fragment complex. Inhibition may also be caused by the substrate nature. It is moreover very difficult to use multi-enzyme systems because of phenomena of enzyme competition with respect to the substrate and because enzyme stability will vary with time.

The invention took advantage of means already known in some other applications and which consist in using enzymatic reactors provided with membranes. Reference may be made for example, to the article by CHEFTEL C. (1972)-Solubilisation enzymatique continue du concentré proétique de poisson. Essai de recyclage des enzymes. Ann. Technol. Agric. 21, (3) 423-433 which describes a membrane-type reactor applied to proteolysis of fish proteic concentrates. The ultrafiltration membrane permits to keep the enzyme in solution in the reactor, as well as the proteic substrate. Only the hydrolysis products, i.e. the peptides, are removed as their formation proceeds. However, in practice, the use of such a reactor is not easy, as pointed out by CHEFTEL. The substrate should be completely solubilizable by the enzyme and the proteic solution has to be of irreproachable bacteriological quality.

As documents showing the state of the art, the following references may further be quoted:

French Patent 74 39311 (publication No. 2,292,435) relates to the obtention of calcium phosphocaseinate from a milk ultrafiltration retentate. The teaching of this patent has therefore for its object production of calcium phosphocaseinate, but without mention of the means to fractionate the latter;

French Patent 77 24069 (publication No. 2,399,213) describes treatment of an hydrolyzate by ultrafiltration, then electrodialysis. This document evidences the fact that it was known to ultrafiltrate a proteic hydrolyzate. The method described in this patent makes it possible to produce a pure solution of natural amino-acids;

The reference CHEMICAL ABSTRACTS, Vol. 87, No. 19, Nov. 7, 1977, page 265, abstract 148 285 p COLUMBUS OH (US) and J. Dairy Research, Vol. 44, No. 2 (1977), pages 373-376, D. W. WEST "A simple method for the isolation of a phosphopeptide from bovine $\alpha$ s$^1$-casein", describes the obtention of a phosphopeptide from caseinate. The method involves enzymatic hydrolysis by trypsine, and fractionating steps by gel filtration and chromatography, but it begins by a reaction with CNBr which leads to quite specific products;

The reference CHEMICAL ABSTRACTS, Vol. 91, No. 21, Nov. 19, 1979, page 523, abstract 173 597 g COLUMBUS OH (US) and Enzyme Microb. Technol., Vol. 1, No. 2 (1979), pages 122-124, J. P. ROOZEN et al. "Enzymic protein hydrolysis in a membrane reactor related to taste properties" describes hydrolysis in an enzymatic reactor, with a view to improve the taste of proteic hydrolyzates. This document thus evidences the fact that the enzymatic reactor is a known apparatus".

The present invention has for its object a method for treating a casein-based raw material wherein the bivalent ions, such as calcium and/or magnesium, are complexed by phosphoserines, as is the case, for example, for milk and for milk ultrafiltration retentate. The method of the invention is based on the fact that phosphoserines have ability to complex alkaline-earth ions, such as calcium and/or magnesium ions, so that, in the products resulting from the enzymatic hydrolysis, the phosphopeptides and non phosphorylated peptides can be separated. Complexing of the bivalent cations facilitates inter-aggregation of the phosphopeptides, which can thus be separated from the non phosphorylated peptides.

Broadly speaking, the invention provides a method for treating a casein-based raw material containing phosphocaseinates of bivalent cations, such as calcium and/or magnesium phosphocaseinates, characterized in that the raw material is subjected to enzymatic hydrolysis by means of a least one proteolytic enzyme capable of reproducing the protein digestion which occurs in vivo in the human body; the thus obtained hydrolyzate is recovered; said hydrolyzate is subjected to at least one ultrafiltration step on membranes able to retain the phosphopeptides, while letting the peptides pass therethrough, the ultrafiltrate thus containing the non phosphorylated peptides; the ultrafiltration retentate is recovered; a treatment is effected to disaggregate the phosphopeptides contained in the retentate; and the latter is subjected to at least one further ultrafiltration step, on membranes which do not retain the phosphopeptides, the latter being thus separated from the enzyme and available to be recovered as a product.

The raw materials liable to be treated by the method of the invention are casein-based materials of any origin, containing phosphocaseinates of bivalent cations. Natural milk provides a valuable source wherein both calcium and magnesium phosphocaseinates are present. A more purified form of raw material suitable for the purposes of the invention consists of a milk ultrafiltration retentate, wherein alkaline earth phosphocaseinates are moreover present. Use may also be made, as a raw material, of phosphocaseinates previously purified by any means known in the art, of the type of the alkaline earth, e.g. magnesium or calcium, phosphocaseinates, which are able to be treated according to the invention.

If a milk ultrafiltration retentate is used as a raw material in the method, the previous ultrafiltration whereby the retentate is produced has not to be pursued to a high concentration level. For example, concentrations levels of the order of 1.5 to 3 are suitable. In practice, a concentration level of the order of 2 is selected. A further possibility is to effect, after ultra filtration proper, a diafiltration whereby the retentate is purified and the proteins dry matter ratio is increased.

Irrespective of its nature, the raw material used is subjected, according to the method of the invention, to enzymatic hydrolysis by means of at least one proteolytic enzyme. As previously mentioned, such an hydrolysis is advantageously effected in a device which combines an ultrafiltration equipment with an enzymatic reactor, this allowing continuous operation.

In such an embodiment, the enzymatic hydrolysis step is effected continuously by feeding the casein-based raw material to a reaction zone so as to bring it into intimate contact with the enzyme, the reaction product is continuously withdrawn by being transferred from the reaction zone to an ultrafiltration zone, wherefrom there is withdrawn, also continuously, a permeate which constitutes the peptidic hydrolyzate.

Within the scope of the method of the invention, the enzymatic hydrolysis step occurs on proteinic solutions wherein the bivalent ions, in particular calcium and/or magnesium, are complexed by the phosphoserines. During enzymatic hydrolysis, the pH should be adjusted in the range of 7 to 9. For this purpose, there is fed, in continuous or discontinuous manner, into the reaction zone a basic compound which may be sodium hydroxide or carbonate, potassium hydroxide or carbonate, calcium hydroxide, ammonium hydroxyde or a mixture thereof. The choice of the particular basic compound will depend upon the purpose intended for the final product.

As an enzyme, use is made preferably of at least one proteolytic enzyme capable of reproducing the proteinic digestion which occurs in vivo in the human body. Therefore, use may be made to advantage of pancreatin, which is a complex mixture containing trypsine, chymotrypsine and other secondary proteolytic enzymes. In practice, it may be resorted to a naturel pancreatic extract commercially available and readily obtainable. However, if so required, use may also be made of enzymes formed by a synthetic mixture, e.g. of alphachymotrypsine and trypsine. Preferably, the synthetic mixture used has a composition approximating that of pancreatin, and therefore including the secondary enzymes contained in natural pancreatic extract. It was found according to the invention that at a pH ranging from 7 to 9, and preferably from 7 to 8.5, e.g. of 8, pancreatin and other similar enzymes meeting the requirements of the invention have maximum stability.

It is further advisable to comply with rather strict temperature conditions in the enzymatic hydrolysis zone. In fact, it was found that enzyme activity was more strongly influenced by the temperature than by the pH. In particular, tests have shown, according to the invention, that with trypsine, the maximum temperature during enzymatic hydrolysis should not be higher than 54° C. and that with chymotrypsine, said temperature should not be higher than 45° C. In practice, when use is made of pancreatin, a compromise will be made taking into account both the optimum conditions for intestinal proteolysis in vivo (temperature of the order of 37° C.) and the fact that higher temperatures are less favorable to germ growth and allow for higher ultrafiltration outputs. In general, the selected temperatures are of the order of 37° to 40° C., and most preferably still close to 37° C.

Obviously, the reaction parameters, viz. the pH and the enzymatic hydrolysis temperature, are interrelated. Thus, it will fall to those skilled in the art to select the most favourable conditions in each particular case.

To effect optimum enzymatic hydrolysis, it is also advisable to select carefully the ultrafiltration membrane to be used in conjunction with the enzymatic reactor. The membranes used may be of any organic or inorganic type. A membrane structure which afforded good results is that of modules with hollow fibers. As a guidance, use may be made of the membranes of Société AMICON available under the trade name H10P5 (cut off threshold 5,000) and H10P10 (cut off threshold 10,000) as well as membranes of Société ROMICON available under the trade name PM2 (cut off threshold 2,000) or PM50 (cut off threshold 50,000). The only requirement to be met is that, in operation, the membrane should retain efficiently the enzyme, while having satisfactory performances, especially as regards its life time.

The method of the invention may be carried out in two separate stages: a first stage consisting of the enzymatic hydrolysis step, and a second stage consisting of the ultrafiltration step associated to said hydrolysis. The equipments for carrying out each of these steps can be separate or integral. However, as an alternate embodiment, the method may also be carried out continuously, both aforesaid stages being effected in a single apparatus. During the initial operating period, e.g. for about one hour, the permeate (liquid flowing through the membrane) is recycled to the hydrolysis zone for the obtention of the desired degree of hydrolysis of the casein-based material. After hydrolysis, the reactor is fed with the casein-based raw material to be treated at a flow-rate identical with that of the permeate.

In practice, there may used crude or skim milk of any origin. Hydrolysis is advantageously effected in an enzymatic reactor at 37° C. in the presence of 2 g per liter of pancreatic enzyme on crude, skim milk, the pH of which is adjusted to 8 by addition of sodium hydroxide.

According to an alternative embodiment the treatment may be applied to a crude, skim milk, previously concentrated by ultrafiltration up to a concentration ratio approximating 2. The pH of this retentate is then raised to a value near 8 by sodium hydroxide addition and said retentate is subjected to hydrolysis in an enzymatic reactor at 37° C. in the presence of 4 g/l of pancreatic enzyme.

After hydrolysis, the residual solution contained in the enzymatic reactor is concentrated by ultrafiltration. At this stage, the solution from the reactor, which contains the enzyme, the non hydrolyzed proteins, the insoluble fractions and the phosphopeptides associated by calcium, is contacted with a membrane able to retain the phosphopeptides while letting the non phosphorylated peptides pass therethrough. For this purpose, use will be made of organic or inorganic membranes of any type, with a cut off threshold ranging from about 2000 to 50,000.

The ultrafiltration step associated with the enzymatic hydrolysis step is advantageously followed by a diafiltration step whereby the non phosphorylated peptidic fraction may be depleted. During diafiltration, the product in contact with the membrane is added with water or a suitable water solution. In practice, it was found that the milk ultrafiltrate prepared during a previous run or coming from another source can advantageously be used as a diafiltration solution. To obtain satisfactory results, the pH of this ultrafiltrate may be raised to values in the range of 7 to 8.

From the previous stages of the method according to the invention, there results on the one hand a fraction (permeate) which comprises the non phosphorylated peptides, and on the other hand a retentate containing the phosphopeptides. As a matter of fact, separation between non phophorylated peptides and phosphopeptides was effected during the enzymatic hydrolysis. The consecutive steps of ultrafiltration and diafiltration afford physical separation of these compounds.

At the following stage of the method of the invention, there is effected a disaggregation treatment of the phosphopeptides contained in the last retentate. According to a practically preferred embodiment, the retentate is acidified so as to solubilize the bivalent ions completed with the phosphopeptides. As an acid, there may be used any inorganic or organic acid suitable for the objects of the present invention and the intended purposes for the products. Therefore, use will be made to advantage of the acids accepted in the alimentation or medical field. Examples of suitable acids are hydrochloric acid, phosphoric acid, sulphuric acid, lactic acid, acetic acid and other similar acids. Good results were obtained with lactic acid. The retentate is acidified until obtention of a pH approximating 4.6, this value ensuring that all the calcium and/or magnesium ions are solubilized.

Alternately, instead of acidification, the phosphopeptide disaggregation can be caused by action of complexing agents for calcium and/or magnesium. In the context of the present invention, the term complexing agents means compounds which are apt to bind calcium and/or magnesium when they are contacted with the phosphopeptides contained in the retentate. Said agents are therefore in general substances exerting a chelating action. Taking into account the intended purposes for the products of the invention, use will be made to advantage of compounds accepted in the alimentation or medical field, especially sodium or potassium citrates.

When starting from a casein-based raw material consisting of crude skim milk or from an ultrafiltration retentate of such a milk, the best results were obtained by acidifying the enzymatic reactor content by means of lactic acid (50%) to a pH of 4.6.

During the last stage of the method of the invention, a fraction containing the phosphopeptides is physically separated by effecting a final ultrafiltration step in such conditions as to obtain, on the one hand, the phosphopeptides and, on the other hand, the by products such as the proteic residues and the residual enzyme. During such stage, it is advantageous that ultrafiltration be followed by diafiltration step, which is known by those skilled in the art, effected to recover the products. In the case of the present stage, diafiltration with pure water proved to be the best.

The phospeptides thus obtained at the end of the method of the invention form the most worthy valuable product. In fact, said product has a high phosphorein content and contains a low amount of aromatic amino-acids (phenylalanine, tyrosine, tryptophane).

The phosphopeptide-rich fraction thus obtained can therefore be characterized both by its particular composition in amino-acids and by a high content of mineral matter (ashes) with respect to the total nitrogen, as the phosphopeptidic fraction contains the whole mineral fraction associated to the caseins in the original raw material (milk or milk retentate).

The main characteristics of the new phosphopeptices according to the invention are defined in Table 1 hereunder.

In the left column of Table 1, the corresponding values for milk are indicated for comparative purposes.

TABLE 1

|  | milk | Non phosphorylated peptides | phospho-peptides |
| --- | --- | --- | --- |
| Total amount of aromatic amino-acids | 12% | >12% | <4% |
| serine | 5,7% | <4% | <20% and >8% |
| Ca + Mg + P $N_T$(1) | 0,07 | <0,02 | >0,2 |

TABLE 1-continued

|  | milk | Non phosphorylated peptides | phospho-peptides |
| --- | --- | --- | --- |
| Free amino-acids | — | <10% | <3% |

(1) $N_T$ = total nitrogen × 6.38

The phosphopeptides obtained by the method of the invention are suitable for numerous applications in the alimentation field.

The products of the invention (phosphopeptides) are useful for alimentation, in particular human alimentation, and for therapeutic nutrition. It is known indeed that, in human milk, the so-called organic phosphorus, i.e. bound to the proteins and bound to the lipids, is comparatively more abundant than in other milks, especially cow's milk. Thus the ratio $$\frac{\text{organic phosphorus}}{\text{total phosphorus}}$$

is of about 0.83 in human milk as against 0.34 in cow's milk. More precisely, the ratio of organic phosphorus bound to the nitrogen versus inorganic phosphorus is about 0.70 in human milk against 0.36 in cow's milk. Therefore, the products of the invention will found applications in the field of so-called milk maternization.

But, in general, it is admitted that the main good property of woman's milk proteins is to ensure a remarkable nitrogen anabolism, together with a renal osmotic load and a $H^+$ ion-load of particularly low values.

Now, this conjunction of a very high nitrogen anabolism with low renal osmotic load and $H^+$ ion-load, is particularly sought in the fields of reanimation and therapeutic nutrition, where high anabolism requirements and functional renal deficiency are quite often coexistent.

The products of the invention are suitable to meet those requirements.

For certain applications, the products of the invention contain an insufficient amount of some essential amino-acids (phenylalanine, tyrosine, tryptophane, cystine). They may then be associated to advantage with other proteins or peptides or either alpha-keto-acid or alpha (OH) acid homologues of essential amino-acids, for restoring of a good amino-acid equilibrium leading to optimal biological value.

It will also be noted that such products (phosphopeptides) have a high affinity for macroelements (calcium, magnesium) and for oligoelements as, particularly, iron, zinc, copper, chrome, nickel, cobalt, manganese and selenium.

The phosphopeptides according to the invention can be advantageously converted into salts of said elements by usual means. Thus, to obtain such an organophosphorated salt, it may be used, as a diafiltration solution when purifying the phosphopeptides, a solution of a salt containing the element to be introduced, e.g. a solution of iron chloride in the case of iron. These organophosphorated salts are highly soluble and they may be advantageously used as carriers for the particular elements. The products of the invention meet the nutritional requirements of patients suffering from pancreatic deficiency, metabolic diseases, nutritional deficiency or distress, which may be or not associated with a functional or organic renal deficiency, in particular when they are associated with peptides, essential amino-acids or essential amino-acid homologues.

The invention therefore finds a direct application in dietetic foods or therapeutic nutriments which are perfectly assimilable by the human body.

Irrespective of the source of proteins, peptides or amino-acids used, these phosphopeptides permit to regulate, in the most desirable manner, the amount of organic phosphorus bound to nitrogen in the formulation to be created.

As it has been previously mentioned, the phosphopeptides according to the invention and their derivatives, notably the organophosphorated salts, which they form with the mineral macroelements, such as calcium and/or magnesium, and/or with oligoelements (Fe, Zn, Cu, Cr, Ni, Co, Mn, Se for instance) find an interesting application in dietetic field.

The invention has also for subject matter dietetic compositions containing an efficient quantity of at least one such phosphopeptide or derivative of phosphopeptide in association with a carrier acceptable from the nutritional point of view. Such an efficient quantity may vary in wide limits according to the effect seeked. For information purpose, a quantity in weight of 10% with respect to the total of the composition is suitable in the usual cases.

The products of the invention can also be applied as such, as medicaments for the man and the animal.

The medicaments concerned are appropriated for alleviating all diseases involving a lack of organic phosphorus and of certain mineral elements. It is given hereafter, for illustration purpose and not at all limitative, some specific examples of such applications.

The mineral derivatives of phosphopeptides according to the invention, consisting of their calcium salts, constitute a protidic mineral supplement rich in organic phosphorus and in calcium. They find an application as medicaments, for instance in the following cases:
  recalcification of the bones after fracture,
  osteoporosis treatment,
  calcic addition during treatment of rickets.

The derivatives of phosphopeptides according to the invention, consisting in their magnesium salts, constitute a mineralo-protidic supplement rich in organic phosphorus and in magnesium. They find an application as medicaments to remedy to all the forms of magnesic deficit, more particularly to the adult, for instance in the following cases:
  needs in Mg greatly increased by the stress
  bad use of Mg food by old people
  increase of Mg needs to the pregnant woman.

Medicaments containing derivatives of phosphopeptides consisting in mixt calcium and magnesium salts, are used in the same way as mineralo-protidic supplement. It goes without saying that similar applications can be foreseen of varied phosphopeptides salts according to the invention, although, in practice calcium and/or magnesium salts are preferred.

It is to be noted that the phosphopeptides, such as they are obtained according to the process of the invention are neutral in the considered pH conditions, for instance at pH close to 4.6. In such conditions, in fact, the cations present in the medium, for instance calcium and/or magnesium, are not linked to the phosphopeptides. However, in the conditions of use, and more particularly when the phosphopeptides are included in dietetic or pharmaceutical compositions, they are found under the form of salts, for instance of calcium and/or magnesium.

The macroelements (preferably calcium and/or magnesium) can be replaced, at least partially, by oligoelements.

The derivatives of phosphopeptides according to the invention which contain oligoelements find an application corresponding to that of particular oligoelements.

The general indications of medicaments containing derivatives of phosphopeptides and oligoelements are among others the digestive bad absorptions inducing lack of oligoelements (Fe, Zn, Cu, Cr, Ni, Mn, Se). Said digestive bad absorptions appear more particularly during inflamatory ileitis, in the case of resect bowels, celiac diseases and radic bowels. As examples, the lack of zinc can cause acrodermatitis enteropathica, diarrhoeas, an increased sensitiveness to infections, hypogonadism. Lacks of iron can entail sideropenic anemia.

The medicaments according to the invention are preferred for the treatment of lack of zinc, copper, chromium and iron.

The invention also concerns pharmaceutical compositions containing a product of the invention in admixture with the usual excipients. Taking into account the physical form of the new product (soluble powder in aqueous medium), the form of presentation does not raise any difficulty. The new products can be ingested or given as such, especially by enteral tract, for instance mixed with usual food. They can also be presented under the form of compositions with usual excipients for instance suitable by oral administration. Appropriated compositions according to the invention can thus be presented under the form of tablets or capsules, with known excipients such as talcum, magnesium, stearate, finely divided silica, and any other similar carrier known by the man skilled in the art.

As example, it has been indicated hereunder a particular case illustrating the preparation of pharmaceutical compositions for administration by oral route. Tablets have been prepared in the usual manner starting with the following formulation:
phosphopeptide (or phosphopeptide salts) according to the invention. 200 mg
excipient QS for a tablet terminated at 300 mg.

The excipient used can be talcum, magnesium stearate or the silica available on the market under the denomination "aerosil".

Capsules dosed at 100 mg of phosphopeptide (or salt) according to the invention and containing a usual excipient QS for a capsule terminated at 200 mg have been prepared in the same manner.

The invention will be further illustrated by the following description and particular examples of carrying it into effect.

The following description will be made with reference to the appended drawings, wherein.

Figure 1:
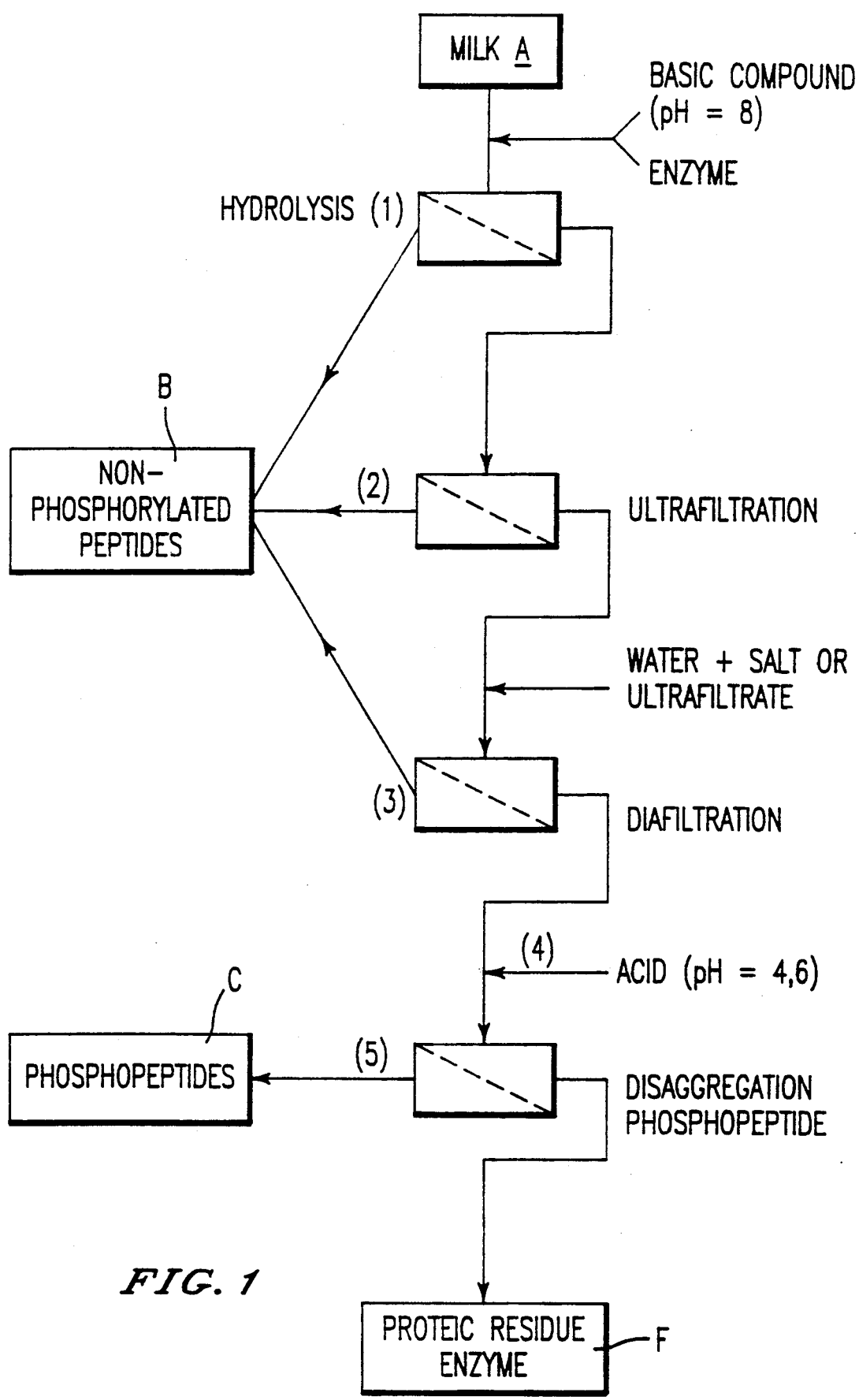
FIG. 1 is a flow-sheet illustrating the method of the invention as applied to a casein-based raw material consisting of milk.

The FIG. 1 is a flow-sheet showing the application of the method of the invention to the treatment of a casein-based raw material consisting of skim crude milk. Said raw material is designated by the reference milk A. According to the invention, the milk is subjected to an enzymatic hydrolysis reaction in the presence of at least one proteolytic enzyme, such a pancreatin, in a basic medium, e.g. at a pH of about 8. The temperature is advantageously of 37° C. The stage of hydrolysis in an enzymatic reactor is designated by reference 1.

At completion of hydrolysis, the reactor solution, containing the enzyme, the non hydrolyzed proteins, the insoluble fractions and the phosphopeptides associated with calcium, was concentrated by the ultrafiltration step (reference 2). Consecutively, diafiltration was effected by contacting the retentate from ultrafiltration 2 while continuously adding thereto a milk ultrafiltrate adjusted at pH 8. The diafiltration step is shown in the drawing by reference 3.

The respective ultrafiltrates from the above steps 1, 2 and 3 are gathered and form together a fraction consisting of non phosphorylated peptides (reference B).

The retentate from ultrafiltration 3 is first treated to disaggregate the phosphopeptides contained therein, advantageously by acidification to pH 4.6, in particular with lactic acid. This step is shown by reference 4. Thereafter, as shown at 5, is the final ultrafiltration step which also includes water diafiltration and at the completion of which separation is effected between, on the one hand, a phosphopeptide fraction C and, on the other hand, a fraction F containing the residual enzyme as well as the proteic residue.

Starting from 1000 liters of milk, in accordance with the flow-sheet in FIG. 1, there may be obtained 900 to 950 liters of peptidic solution at 27 g/liter and about 50 liters of phosphopeptides at 80 g/liter.

Figure 2:
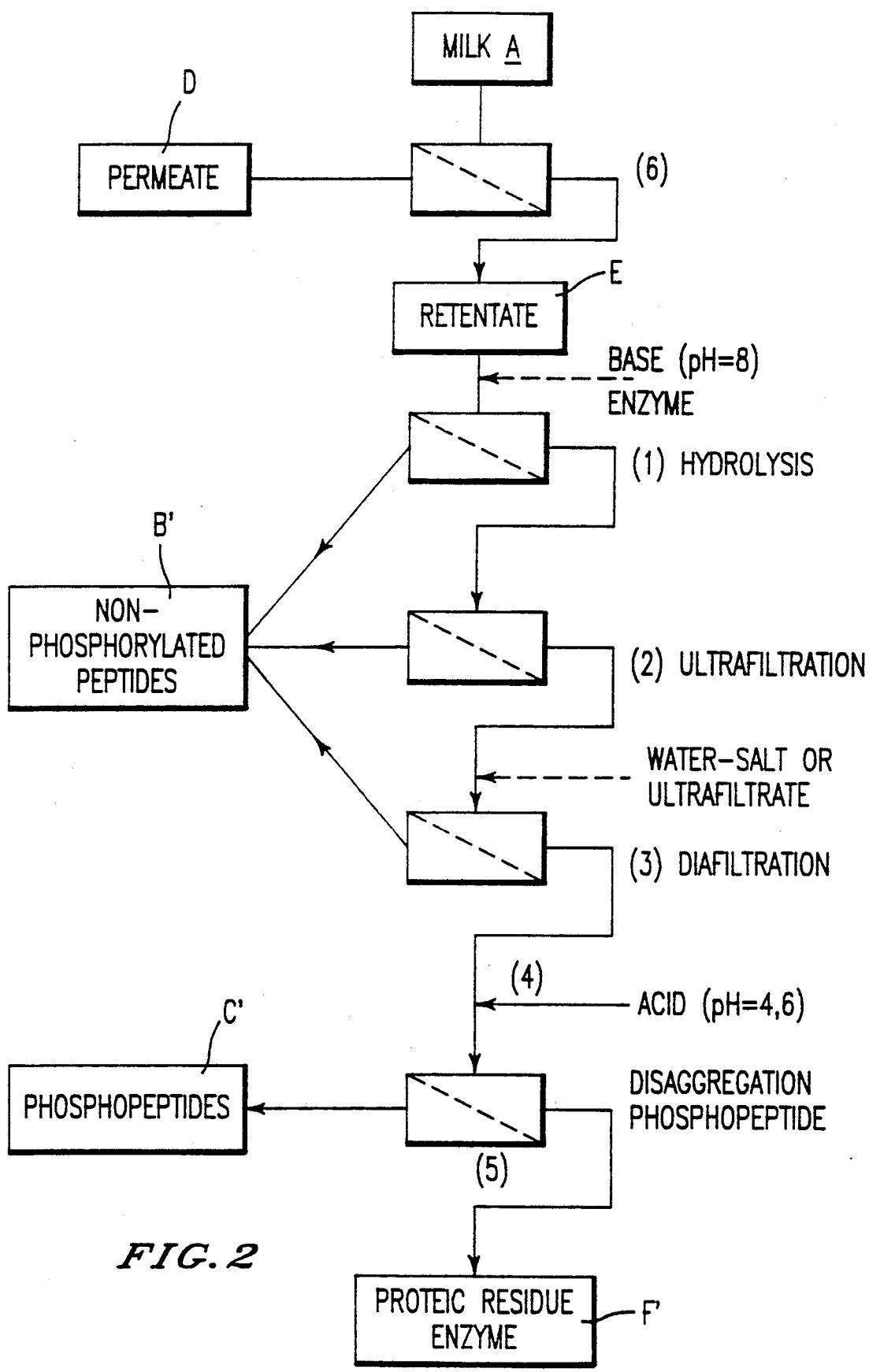
FIG. 2 is a flow-sheet similar to that of FIG. 1 showing the application of the method of the invention to a milk ultrafiltration retentate.

In the alternate embodiment shown in FIG. 2, the crude skim milk A is first subjected to ultrafiltration (shown at 6) up to a concentration ratio of about 2. Thus, a permeate D and a retentate E are separated. It is the retentate which is then used as a casein-based raw material. Retentate E is brought to pH 8 by addition of a basic compound, and hydrolyzed in an enzymatic reactor in the presence of a proteolytic enzyme (e.g. with 4 g/liter of pancréatic enzyme at a temperature of 37° C.). As in FIG. 1, the hydrolysis step is shown at 1. At completion of hydrolysis, the residual solution from the enzymatic reactor was concentrated by ultrafiltration (reference 2), then diafiltrated (reference 3) with ultrafiltrate at pH 7.0 so as to exhaust the non phosphorylated peptidic fraction. The various ultrafiltrates from ultrafiltrations 1, 2 and 3 are gathered and form the non phosphorylated peptidic fraction B'.

As in the case of FIG. 1, the reactor content is subjected to a treatment for disaggregating the phosphopeptides, advantageously an acidification to a pH of 4.6, for instance by addition of lactic acid at 50% (reference 4). The solution contained in the reactor is then subjected to ultrafiltration and water diafiltration, both shown by reference 5, whereby the phosphopeptides (C') can be separated from a residual proteic-enzyme fraction (F').

By complying with the reaction flow-sheet in FIG. 2, and starting from 1000 liters of milk, there may be obtained 400 to 450 liters of peptidic solution (57 g/liter) and about 50 liters of phosphopeptide solution (80 g/liter).

Figure 3:
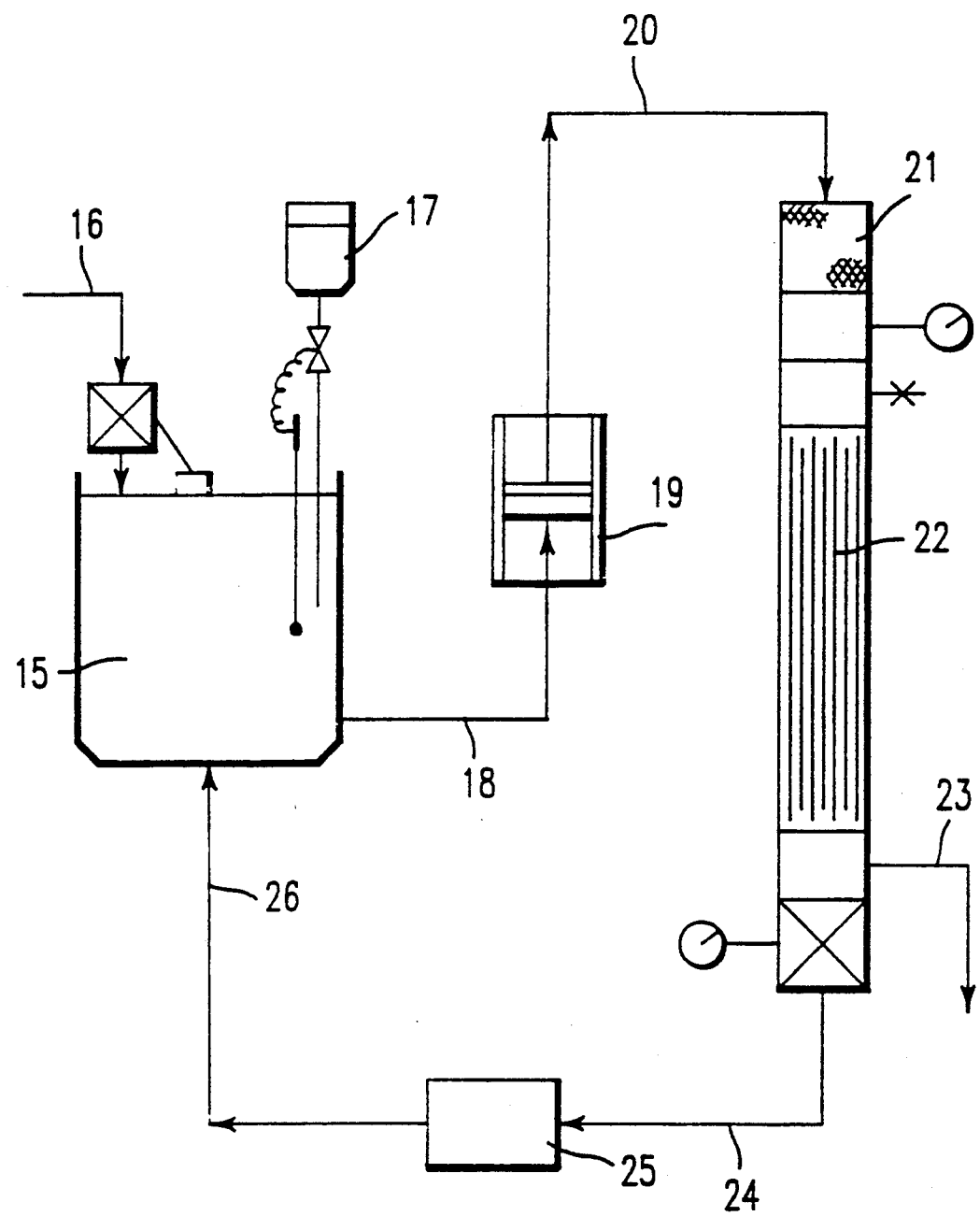
FIG. 3 is a diagrammatic view of the membrane-type enzymatic reactor which may be used to meet the requirements of the invention.

FIG. 3 shows a membrane-type enzymatic reactor which may be used in the method of the invention.

Said reactor includes first a reaction tank generally designated by reference 15. Continuous feeding of phosphocaseinates occurs through duct 16. A device 17 serves both to measure the pH and to keep it constant in the reaction tank by neutralizing the $H^+$ ions released when the peptidic bonds are broken. Said device was a Mettler pH-stat comprising a potential amplifier, an equivalence point presetting switch and an automatic burette for feeding the reactive, the latter being a basic compound such as mentioned above. No excessive electrode fouling was noted. The hydrolysis product withdrawn from the reaction tank through duct 18 is conveyed by an automatic membrane-type pump 19. A practical example is the pump of AMICON LP 20 A model, with an output of 720 l/h at 25 psi. At the outlet of the pump, the product flows through a duct 20 and is fed onto a pre-filter 21 having a pore size of 150 microns. Reference 22 designates the ultrafiltration module. In a specific example, the system used was AMICON DC 10 S model having ultrafiltration cartridges of the hollow fiber type. The permeate was recovered through a duct 23 and formed the desired peptidic hydrolyzate. The retentate was withdrawn from module 22 through duct 24, then fed to an exchanger 25 and conveyed through duct 26 to be recycled into reaction tank 15.

The membranes used were of the hollow fiber type having the following characteristics:

TABLE II

| Type | Cut-off threshold | area | Manufacturer |
|---|---|---|---|
| H 10 P 5 | 5,000 | 0,9 $m^2$ | Amicon |
| H 10 P 10 | 10,000 | | |
| PM 2 | 2,000 | 1,4 $m^2$ | Romicon |
| PM 50 | 50,000 | | |

EXAMPLE 1

This example relates to the use of milk as raw material.

After being skimmed, the crude milk was hydrolyzed in an enzymatic reactor identical with that shown in FIG. 3; the membranes used was of the XM 50 type (hollow fibers). The enzyme (a pancreation of bovire origin having an activity of 4 NF was of SIGMA origin and its concentration was of 2 g/liter. The pH in the reactor was kept at 8 by addition of sodium hydroxide 2N. Hydrolysis was effected at 37° C.

The ultrafiltrate collected during hydrolysis formed the fraction of non phosphorylated peptides. At completion of hydrolysis, the reactor content was concentrated (3.4 times) so as to reduce the volume subject to diafiltration. Diafiltration was effected with ultrafiltrate obtained by milk treatment on membrane XM 50 at 25° C. and brought to pH 8 with sodium hydroxide 2N. The diafiltration purpose was to deplete reactor content of non phosphorylated peptides. The residual solution from the enzymatic reactor, containing the enzyme and the aggregated phosphopeptides, was then acidified to pH 4.6 by addition of 50% lactic acid. The disintegrated phosphopeptides were collected in the permeate.

The chemical analysis of the various products of this production run are gathered in the following Tables III and IV.

TABLE III

| | Chemical composition (g/kg) | | | |
|---|---|---|---|---|
| | D.E.* | $N_T$** | Ca | P |
| Starting milk | 90.0 | 29.3 | 1.20 | 1.02 |

TABLE III-continued

| | Chemical composition (g/kg) | | | |
|---|---|---|---|---|
| | D.E.* | $N_T$** | Ca | P |
| Reactor content at completion of hydrolysis | 88.5 | 31.2 | 1.20 | 1.02 |
| Reactor content concentrated by ultrafiltration | 112.4 | 40.7 | 3.81 | 2.65 |
| Reactor content after diafiltration | 87.0 | 14.4 | 4.17 | 3.08 |
| Non phosphorylated peptides | 80.0 | 27.0 | 0.14 | 0.35 |
| Phosphopeptides | 89.0 | 8.2 | 3.40 | 2.40 |

*D.E. = dry extract
**$N_T$ = total nitrogen × 6.38

EXAMPLE 2

This example relates to the use of milk ultrafiltration retentate as a raw material.

After being skimmed, the crude milk was concentrated (2 times) by ultrafiltration at 25° C. on a XM 50 membrane. The retentate pH was then adjusted to 8 by addition of sodium hydroxide 2N. The retentate was thereafter hydrolyzed in the enzymatic reactor (FIG. 3). The enzyme has a nature identical with that used in Example 1 and a concentration of 4 g/liter. Hydrolysis was effected at 37° C. and the pH was kept at 8 by addition of sodium hydroxide 2N.

TABLE IV

| | Composition in amino-acids | | | |
|---|---|---|---|---|
| | Non phosphorylated peptides | phosphopeptides | Non phosphorylated peptides | Phosphopeptides |
| Asp | 6.92 | 9.22 | Cys | 0.68 | ε |
| Thr | 3.55 | 4.50 | Met | 2.01 | 0.58 |
| Ser | 3.58 | 11.80 | Ile | 4.42 | 7.58 |
| Pro | 9.07 | 5.88 | Leu | 8.92 | 4.95 |
| Glu | 19.40 | 30.80 | Tyr | 4.92 | <2 |
| Gly | 1.71 | 2.38 | Phe | 4.46 | 1.80 |
| Ala | 2.83 | 2.96 | Lys | 7.56 | 4.57 |
| Val | 5.57 | 7.12 | His | 2.60 | 1.37 |
| | | | Arg | 3.09 | 1.96 |

The ultrafiltrate collected during hydrolysis formed the non phosphorylated peptide fraction. When hydrolysis was completed, the enzymatic reactor content was concentrated 3 times by ultrafiltration; diafiltration was effected in this case with milk ultrafiltrate, pH 7, so as to deplete the reactor solution of non phosphorylated peptides. The reactor content was then acidified to pH 4.6 with 50% lactic acid. The disaggregated phosphopeptides were thereafter collected from the permeate.

The chemical analyses and composition in aminoacids of the various products thus obtained are shown in Tables V and VI given below.

Illustrative examples relating to applications of products of the invention will be given hereunder, but are not limitative of the invention.

EXAMPLE 3

This example relates to a reanimation product intended for enteral administration to patients requiring a proteic input of the order of 7-15% of the Total Calorific Input (TCI), e.g. suffering from the following ailments: mucoviscidose or pancreas cystic fibrosis, renal deficiency, patients with an infectious or inflammatory disease of the intestinal membrane, nutritional distress requiring intense anabolism, with reduced osmotic renal load and $H^+$ ion-load. These proteins are preferably brought into a pre-digested state.

TABLE V

| | Chemical composition (g/kg) | | | |
|---|---|---|---|---|
| | D.E. | $N_T$ | Ca | P |
| Milk | 90.0 | 30.0 | 1.15 | 1.00 |
| Retentate | 122.9 | 59.8 | 1.90 | 1.63 |
| Reactor content upon hydrolysis completion after ultrafiltration | 148.5 | 73.5 | 5.09 | 3.97 |
| Reactor content after diafiltration | 80.0 | 14.34 | 3.39 | 2.70 |
| Non phosphorylated peptides | 104.0 | 53.3 | 0.20 | 0.40 |
| Phosphopeptides | 74.3 | 7.5 | 2.55 | 1.69 |

TABLE VI

| | COMPOSITION IN AMINO-ACIDS | | | |
|---|---|---|---|---|
| | Non phosphorylated peptides | phosphopeptides | Non phosphorylated peptides | Phosphopeptides |
| Asp | 7.32 | 8.02 | Cys | 0.66 | ε |
| Thr | 4.56 | 4.42 | Met | 2.44 | 1.49 |
| Ser | 3.97 | 11.98 | Ile | 4.73 | 7.71 |
| Pro | 9.30 | 5.29 | Leu | 9.70 | 5.17 |
| Glu | 20.61 | 26.50 | Tyr | 5.20 | 1.25 |
| Gly | 1.88 | 2.73 | Phe | 4.88 | 1.80 |
| Ala | 3.16 | 3.15 | Lys | 7.79 | 4.90 |
| Val | 5.95 | 7.42 | His | 2.84 | 1.47 |
| | | | Arg | 3.74 | 2.10 |

Example of a pharmaceutical composition:

mixture of small peptides according to the invention:

Phosphopeptides from 4 to 8%
Lactoserum peptides 60%
casein peptides from 32 to 36%
CMP from 0 to 4%  } 2.50 g lipids:
mixture in equal parts of:
butter oil 0.5 g
medium chain triglycerides (MCT) 0.5 g
maize oil 0.5 g
sunflower oil 0.5 g
glycerol monostearate 2.1 g  } 4.10 g glucids:
glucose polymers 10 g
glucose 1.5 g
galactose 1.5 g  } 13.00 g vitamins:
A, D, E, $B_1$, $B_2$, PP, $B_5$
$B_6$, $B_{12}$, folic acid,
Biotine, Vit. C  } according to FAO/MWO recommendations mineral elements:
(calcium, sodium, potassium, magnesium, phosphorus, zinc, iron, copper, manganese, chlorine, iodine  } 0.455 g distilled water  as required for 100 g

EXAMPLE 4

This example relates to a reanimation product for enteral administration to patients requiring a proteic input of the order of 12-25% of the Total Calorific Input, under the form of proteins. Such an alimentation is appropriate for any situation requiring substantial nitrogen anabolism and an extra supply or organic $P^-$.

Example of a pharmaceutical composition mixture of small peptides according to the invention:

| Example of a pharmaceutical composition | |
| --- | --- |
| phosphopeptides from 8 to 28% | from |
| lactoserum peptides from 22 to 60% | 3 to |
| Casein peptides from 12 to 70% | 6.25 g |
| lipids: | |
| M.C.T 2.30 g | |
| oil with high content in | |
| essential fatty acids 0.50 g | 2.90 g |
| emulsifier 0.10 g | |
| glucids: | |
| small glucose polymers from 8.25 to 10.5 g | from |
| glucose from 2 to 2.5 g | 12.25 to |
| galactose from 2 to 2.5 g | 15.5 g |
| vitamins: | |
| A, D, E, $B_1$, $B_2$, | according to |
| PP, $B_5$, $B_6$, | FAO/MWO |
| $B_{12}$, folic acid, | recom- |
| Biotine, C Vitamin | mendations |
| mineral elements: | |
| (calcium, sodium, potassium, magnesium | |
| phosphorus, zinc, iron, copper, manganese, chlorine, iodine) | 0.455 g |
| distilled water | as required for 100 g |

EXAMPLE 5

This example relates to a reanimation product intended for enteral administration to patients requiring an proteic input of the order of 7–12% of the T.C.I., in particular in the following affections: mucoviscidose or pancreas cystic fibrosis, renal deficiency, patients having an infectious or inflammatory disease of the intestinal membrane, nutritional distress requiring intense anabolism and osmotic renal overload with a reduced $H^+$ ion load. The proteins are preferably brought into a pre-digested form.

| Example of a pharmaceutical composition: | |
| --- | --- |
| Mixture of small peptides according to the invention | |
| phosphopeptides 4% | |
| casein peptides 36% | 2.50 g |
| lactoserum peptides 40% | |
| CMP 20% | |
| lipids | |
| mixture in equal parts of: | |
| butter oil 0.5 g | |
| MCT 0.5 g | |
| maize oil 0.5 g | 4.10 g |
| sunflower oil 0.5 g | |
| glycerol monostearate 2.1 g | |
| glucids | |
| glucose polymers 10 g | |
| glucose 1.5 g | 13.00 g |
| galactose 1.5 g | |
| vitamins | |
| A, D, E, $B_1$, $B_2$, PP, | according to |
| $B_5$, $B_6$, $B_{12}$ | FAO/MWO |
| folic acid, Biotine, C vitamin | recommendations |
| mineral elements | |
| (calcium, sodium, potassium, magnesium, | |
| phosphorus, zinc, iron, copper, manganese, chlorine, iodine | 0.455 g |
| distilled water | as required for 100 g |

The peptide mixture containing the phosphopeptides of the invention may include to advantage the peptides obtained in accordance with the method described in French patent application filed on Jun. 26, 1979 under No. 79 16, 483 in the name of Institut National de la Recherche Agronomique for "Hydrolysat enzymatique total de proteines de lactoserum, obtention et applications". It will be recalled that such a peptidic hydrolyzate is substantially free of residual proteins and that 50% of the peptides contain 2 to 5 amino-acids. More particularly, said hydrolyzate contains 70 to 90% of the nitrogen present as peptides having a number of amino-acids lower than 10. Under a specific form, the hydrolyzate corresponds to the following aminogram:

| Aminogram: | | | |
| --- | --- | --- | --- |
| Ile | 6.0 | Arg | 2.7 |
| Leu | 9.9 | His | 1.7 |
| Lys | 9.2 | Ala | 4.9 |
| Cys | 1.8 | Asp | 9.5 |
| Phe | 3.2 | Glu | 17.6 |
| Thr | 6.7 | Gly | 1.7 |
| Tyr | 3.6 | Pro | 6.2 |
| Trp | 2.0 | Ser | 5.5 |
| Val | 5.5 | Met | 2.0 |

The procedure for obtaining such an hydrolyzate is to effect first ultrafiltration of the lactoserum, then enzymatic hydrolysis thereof, and is more particularly characterized in that the ultrafiltration retentate is contacted with an enzyme able to reproduce the proteic digestion occurring in vivo in the human body, said enzyme being preferably pancreatin, hydrolysis being carried on until the product contains no more residual proteins, i.e. is free of any nitrogen which can be precipitated by trichloroacetic acid, 12%, and thereafter recovering the thus obtained hydrolyzate which constitutes the total enzymatic hydrolyzate desired.

What we claim is:

1. An essentially pure non-phosphorylated casein peptide, which comprises greater than 12% by weight of aromatic amino acids, less than 4% by weight of serine, less than 10% by weight of free amino acids, and a value of less than 0.02 for the formula:

$$\frac{Ca + Mg + P}{N_T}$$

wherein Ca is total calcium, Mg is total magnesium, P is total phosphorus, and $N_T$ is total nitrogen $\times 6.38$.

2. The essentially pure non-phosphorylated casein peptide of claim 1, which has the following composition of amino acids: Asp, 6.92; Thr, 3.55; Ser, 3.58; Pro, 9.07; Glu, 19.40; Gly, 1.71; Ala, 2.83; Val, 5.57; Cys, 0.68; Met, 2.01; Ile, 4.42; Leu, 8.92; Tyr, 4.98; Phe, 4.46; Lys, 7.56; His, 2.60 and Arg, 3.09.

3. A method for obtaining a non-phosphorylated peptide, which peptide comprises greater than 12% by weight of aromatic amino acids, less than 4% by weight of serine, less than 10% by weight of free amino acids, and a value of less than 0.02 for the formula:

$$\frac{Ca + Mg + P}{N_T}$$

wherein Ca is total calcium, Mg is total magnesium, P is total phosphorus, and $N_T$ is total nitrogen $\times 6.38$, or a pharmaceutically acceptable salt thereof; which method comprises:

a) subjecting a casein-based raw material to enzymatic hydrolysis by means of at least one proteolytic enzyme capable of reproducing the proteic digestion which occurs in vivo in the human body;

b) recovering the resulting hydrolyzate and subjecting the same to at least one ultrafiltration step on membranes capable of retaining phosphopeptides while letting the non-phosphorylated peptides pass therethrough; and c) recovering the non-phosphorylated peptides from the ultrafiltrate.

4. The method according to claim 3, wherein said casein-based raw material is selected from the group consisting of milk and a milk ultrafiltration retentate.

5. The method according to claim 3, wherein said enzymatic hydrolysis is effected in a device which combines an ultrafiltration equipment with an enzymatic reactor, thus forming an enzymatic reactor with a membrane.

6. The method according to claim 3, wherein said enzymatic hydrolysis is effected continuously by feeding the casein-based raw material to a reaction zone to bring it into intimate contact with the enzyme, the reaction product being continuously withdrawn and transferred from the reaction zone to an ultrafiltration zone, wherefrom there is withdrawn continuously a permeate which forms the peptidic hydrolysis.

7. The method according to claim 3, wherein the pH is adjusted to a range of 7 to 9 for effecting said enzymatic hydrolyzate.

8. The method according to claim 3, wherein said enzyme is selected from the group consisting of a pancreatin in the form of a natural pancreatic extract, and synthetic mixtures of trypsin and α-chymotrypsin.

9. The method according to claim 3, wherein said enzymatic hydrolysis is effected at a temperature in the range of 37° to 45° C.

10. The method according to claim 9, wherein said enzymatic hydrolysis is effected at a temperature in the range of 37° to 40° C.

11. The method according to claim 10, wherein said enzymatic hydrolysis is effected at a temperature of about 37° C.

* * * * *